US 10,716,759 B2

(12) United States Patent
Tyavanagimatt et al.

(10) Patent No.: US 10,716,759 B2
(45) Date of Patent: *Jul. 21, 2020

(54) REHYDRATION OF MICRONIZED TECOVIRIMAT MONOHYDRATE

(71) Applicant: SIGA TECHNOLOGIES, INC., Corvallis, OR (US)

(72) Inventors: Shanthakumar R. Tyavanagimatt, Corvallis, OR (US); Matthew Reeves, Albany, OR (US); N K Peter Samuel, Corvallis, OR (US); Steven Priebe, Plesanton, CA (US); Ying Tan, Walnut Creek, CA (US); Dennis E. Hruby, Albany, OR (US)

(73) Assignee: SIGA TECHNOLOGIES INC., Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/519,815

(22) Filed: Jul. 23, 2019

(65) Prior Publication Data
US 2019/0380966 A1 Dec. 19, 2019

Related U.S. Application Data

(62) Division of application No. 15/027,557, filed as application No. PCT/US2014/065674 on Nov. 14, 2014, now Pat. No. 10,406,103.

(60) Provisional application No. 61/906,119, filed on Nov. 19, 2013.

(51) Int. Cl.
A61K 9/16 (2006.01)
A61K 31/4035 (2006.01)
A61K 31/403 (2006.01)

(52) U.S. Cl.
CPC .......... A61K 9/1688 (2013.01); A61K 31/403 (2013.01); A61K 31/4035 (2013.01)

(58) Field of Classification Search
None
See application file for complete search history.

(56) References Cited

U.S. PATENT DOCUMENTS

| 2006/0111354 | A1 | 5/2006 | Serno et al. | |
| 2008/0004452 | A1 | 1/2008 | Jordan et al. | |
| 2011/0236434 | A1* | 9/2011 | Tyavanagimatt | A61K 9/1652 424/400 |

FOREIGN PATENT DOCUMENTS

| CN | 1681481 A | 10/2005 |
| CN | 101445478 A | 6/2009 |
| CN | 103068232 A | 4/2013 |
| JP | 2009507051 A | 2/2009 |
| JP | 2011041888 A * | 3/2011 |
| WO | WO2007/065448 A1 | 6/2007 |
| WO | WO-2008-079159 A2 | 7/2008 |
| WO | WO-2008-130348 A1 | 10/2008 |
| WO | WO-2012-018810 A1 | 2/2012 |

OTHER PUBLICATIONS

International Search Report issued in PCT/US2014/65674, dated Jan. 27, 2015.
Notification Concerning Transmittal of International Preliminary Report on Patentability (Chapter I of the Patent Cooperation Treaty) issued in PCT/US2014/065674 dated Jan. 27, 2015.
European Search Report issued in European Application No. 14863672.3, dated Apr. 6, 2017.
Chinsangaram, J. et al. "Pharmacokinetic Comparison of a Single Oral Dose of Polymorph Form I versus Form V Capsules of the Antiorthopoxvirus Compound ST-246 in Human Volunteers", Antimicrobial Agents and Chemotherapy, vol. 56, No. 7, Jul. 2012, pp. 3582-358.
Office Action issued in Chinese Counterpart Application 201480056338.7 dated Jan. 19, 2018.
Office Action issued in Japanese Counterpart Application No. 2016-522728 dated Jul. 9, 2018.
Kang, Crystal Growth & Design, 12 2012, (Year: 2012).
Office Action issued in Chinese Counterpart Application 201480056338.7 dated Jan. 26, 2018.
Office Action issued in Chinese Counterpart Application 201480056338.7 dated Oct. 26, 2018.
Office Action issued in Israel Counterpart Application No. 244731 dated Dec. 27, 2018.
Australian Examination Report issued in counterpart Australian Application No. 201435323 dated Feb. 5, 2019.
CN 101445478 machine translation from WIPO, 2009 (Year: 2009).
Australian Examination Report issued in counterpart AU application No. 2019208252, dated Jan. 20, 2020.

* cited by examiner

Primary Examiner — Susan T Tran
Assistant Examiner — William Craigo
(74) Attorney, Agent, or Firm — Charles C. Achkar; Ostrolenk Faber LLP.

(57) ABSTRACT

Disclosed are methods for hydration of ST-246 particles comprising exposing said particles to moisture by conveying volumes of air containing moisture.

5 Claims, No Drawings

REHYDRATION OF MICRONIZED TECOVIRIMAT MONOHYDRATE

CROSS REFERENCE TO RELATED APPLICATIONS

The present application is a divisional application of U.S. patent application Ser. No. 15/027,557 filed Apr. 6, 2016, which is a § 371 National Phase Application of International Application No. PCT/US2014/065674 filed Nov. 14, 2014, which claims the benefit of U.S. Provisional Patent Application No. 61/906,119, filed on Nov. 19, 2013, the disclosure of which are hereby fully incorporated by reference.

STATEMENT REGARDING FEDERALLY SPONSORED RESEARCH OR DEVELOPMENT

This invention was made with U.S. government support under Contract No.: HES0100201100001C awarded by the Biomedical Advanced Research and Development Authority (BARDA). The US government has certain rights in this invention.

FIELD OF THE INVENTION

Described herein are methods for the preparation of stable micronized monohydrate form of Tecovirimat and its use for the treatment or prophylaxis of viral infections and diseases associated therewith, particularly those viral infections and associated diseases caused by the orthopoxvirus. Tecovirimat, with a proprietary name of ST-246®, has a chemical name of N-[(3aR,4R,4aR,5aS,6S,6aS)-3,3a,4,4a,5,5a,6,6a-octahydro-1,3-dioxo-4,6-ethenocycloprop[f]isoindol-2 (1H)-yl]-4-(trifluoromethyl)-benzamide.

BACKGROUND OF THE INVENTION

The Orthopox genus (Orthopoxviridae) is a member of the Poxviridae family and the Choropoxivirinae subfamily. The genus consists of numerous viruses that cause significant disease in human and animal populations. Viruses in the orthopox genus include cowpox, monkeypox, vaccinia, and variola (smallpox), all of which can infect humans.

The smallpox (variola) virus is of particular importance. Recent concerns over the use of smallpox virus as a biological weapon have underscored the necessity of developing small molecule therapeutics that target orthopoxviruses. Variola virus is highly transmissible and causes severe disease in humans resulting in high mortality rates (Henderson et al. (1999) JAMA. 281:2127-2137). Moreover, there is precedent for use of variola virus as a biological weapon. During the French and Indian wars (1754-1765), British soldiers distributed blankets used by smallpox patients to American Indians in order to establish epidemics (Stern, E. W. and Stern, A. E. 1945. The effect of smallpox on the destiny of the Amerindian. Boston). The resulting outbreaks caused 50% mortality in some Indian tribes (Stern, E. W. and Stern, A. E.). More recently, the Soviet government launched a program to produce highly virulent weaponized forms of variola in aerosolized suspensions (Henderson, supra). Of more concern is the observation that recombinant forms of poxvirus have been developed that have the potential of causing disease in vaccinated animals (Jackson et al. (2001) J. Virol., 75:1205-1210).

The smallpox vaccine program was terminated in 1972; thus, many individuals are no longer immune to smallpox infection. Even vaccinated individuals may no longer be fully protected, especially against highly virulent or recombinant strains of virus (Downie and McCarthy. (1958) J Hyg. 56:479-487; Jackson, supra). Therefore, mortality rates would be high if variola virus were reintroduced into the human population either deliberately or accidentally.

Variola virus is naturally transmitted via aerosolized droplets to the respiratory mucosa where replication in lymph tissue produces asymptomatic infection that lasts 1-3 days. Virus is disseminated through the lymph to the skin where replication in the small dermal blood vessels and subsequent infection and lysis of adjacent epidermal cells produces skin lesions (Moss, B. (1990) Poxviridae and Their Replication, 2079-2111. In B. N. Fields and D. M. Knipe (eds.), Fields Virology. Raven Press, Ltd., New York). Two forms of disease are associated with variola virus infection; variola major, the most common form of disease, which produces a 30% mortality rate and variola minor, which is less prevalent and rarely leads to death (<1%). Mortality is the result of disseminated intravascular coagulation, hypotension, and cardiovascular collapse, which can be exacerbated by clotting defects in the rare hemorrhagic type of smallpox (Moss, supra).

A recent outbreak of monkeypox virus underscores the need for developing small molecule therapeutics that target viruses in the orthopox genus. Appearance of monkeypox in the US represents an emerging infection. Monkeypox and smallpox cause similar diseases in humans, however mortality for monkeypox is lower (1%).

Vaccination is the current means for preventing orthopox virus disease, particularly smallpox disease. The smallpox vaccine was developed using attenuated strains of vaccinia virus that replicate locally and provide protective immunity against variola virus in greater than 95% of vaccinated individuals (Modlin (2001) MMWR (Morb Mort Wkly Rep) 50:1-25). Adverse advents associated with vaccination occur frequently (1:5000) and include generalized vaccinia and inadvertent transfer of vaccinia from the vaccination site. More serious complications such as encephalitis occur at a rate of 1:300,000, which are often fatal (Modlin, supra). The risk of adverse events is even more pronounced in immunocompromised individuals (Engler et al. (2002) J Allergy Clin Immunol. 110:357-365). Thus, vaccination is contraindicated for people with AIDS or allergic skin diseases (Engler et al.). While protective immunity lasts for many years, the antibody response to smallpox vaccination is significantly reduced 10 to 15 years post inoculation (Downie, supra). In addition, vaccination may not be protective against recombinant forms of orthopoxvirus. A recent study showed that recombinant forms of mousepox virus that express IL-4 cause death in vaccinated mice (Jackson, supra). Given the side effects associated with vaccination, contraindication of immunocompromised individuals, and inability to protect against recombinant strains of virus, better preventatives and/or new therapeutics for treatment of smallpox virus infection are needed.

Vaccinia virus immunoglobulin (VIG) has been used for the treatment of post-vaccination complications. VIG is an isotonic sterile solution of immunoglobulin fraction of plasma derived from individuals who received the vaccinia virus vaccine. It is used to treat eczema vaccinatum and some forms of progressive vaccinia. Since this product is available in limited quantities and difficult to obtain, it has not been indicated for use in the event of a generalized smallpox outbreak (Modlin, supra).

Cidofovir ([(S)-1-(3-hydroxy-2-phosphonylmethoxypropyl)cytosine] [HBMPC]) is a nucleoside analog approved for treatment of CMV retinitis in AIDS patients. Cidofovir has been shown to have activity in vitro against a number of DNA containing viruses including adenovirus, herpesviruses, hepadnaviruses, polyomaviruses, papillomaviruses, and orthopoxviruses (Bronson et al. (1990) Adv. Exp. Med. Biol. 278:277-83; De Clercq et al. (1987) Antiviral Res. 8:261-272; de Oliveira et al. (1996) Antiviral Res. 31:165-172; Snoeck et al. (2001) Clin Infect. Dis. 33:597-602). Cidofovir has also been found to inhibit authentic variola virus replication (Smee et al. (2002) Antimicrob. Agents Chemother. 46:1329-1335).

However, cidofovir administration is associated with a number of issues. Cidofovir is poorly bioavailable and must be administered intravenously (Laezari et al. (1997) Ann. Intern. Med. 126:257-263). Moreover, cidofovir produces dose-limiting nephrotoxicity upon intravenous administration (Lalezari et al.). In addition, cidofovir-resistance has been noted for multiple viruses. Cidofovir-resistant cowpox, monkeypox, vaccinia, and camelpox virus variants have been isolated in the laboratory by repeated passage in the presence of drug (Smee, supra). Cidofovir-resistance represents a significant limitation for use of this compound to treat orthopoxvirus replication. Thus, the poor bioavailability, need for intravenous administration, and prevalence of resistant virus underscores the need for development of additional and alternative therapies to treat orthopoxvirus infection.

In addition to viral polymerase inhibitors such as cidofovir, a number of other compounds have been reported to inhibit orthopoxvirus replication (De Clercq. (2001) Clin Microbiol. Rev. 14:382-397). Historically, methisazone, the prototypical thiosemicarbazone, has been used in the prophylactic treatment of smallpox infections (Bauer et al. (1969) Am. J Epidemiol. 90:130-145). However, this compound class has not garnered much attention since the eradication of smallpox due to generally unacceptable side effects such as severe nausea and vomiting. Mechanism of action studies suggest that methisazone interferes with translation of L genes (De Clercq (2001), supra). Like cidofovir, methisazone is a relatively non-specific antiviral compound and can inhibit a number of other viruses including adenoviruses, picornaviruses, reoviruses, arboviruses, and myxoviruses (Id.).

Another class of compounds potentially useful for the treatment of poxviruses is represented by inhibitors of S-adenosylhomocysteine hydrolase (SAH). This enzyme is responsible for the conversion of S-adenosylhomocysteine to adenosine and homocysteine, a necessary step in the methylation and maturation of viral mRNA. Inhibitors of this enzyme have shown efficacy at inhibiting vaccinia virus in vitro and in vivo (De Clercq et al. (1998) Nucleosides Nucleotides. 17:625-634). Structurally, all active inhibitors reported to date are analogues of the nucleoside adenosine. Many are carbocyclic derivatives, exemplified by Neplanacin A and 3-Deazaneplanacin A. While these compounds have shown some efficacy in animal models, like many nucleoside analogues, they suffer from general toxicity and/or poor pharmacokinetic properties (Coulombe et al. (1995) Eur. J Drug Metab Pharmacokinet. 20:197-202; Obara et al. (1996) J Med. Chem. 39:3847-3852). It is unlikely that these compounds can be administered orally, and it is currently unclear whether they can act prophylactically against smallpox infections. Identification of non-nucleoside inhibitors of SAH hydrolase, and other chemically tractable variola virus genome targets that are orally bioavailable and possess desirable pharmacokinetic (PK) and absorption, distribution, metabolism, excretion (ADME) properties would be a significant improvement over the reported nucleoside analogues. In summary, currently available compounds that inhibit smallpox virus replication are generally non-specific and suffer from use limiting toxicities and/or questionable efficacies.

In U.S. Pat. No. 6,433,016 (Aug. 13, 2002) and U.S. Application Publication 2002/0193443 A1 (published Dec. 19, 2002) a series of imidodisulfamide derivatives are described as being useful for orthopoxvirus infections.

New therapies and preventatives are clearly needed for infections and diseases caused by orthopoxvirus infection.

The co-owned PCT publication WO 2004/112718 (published Dec. 29, 2004) discloses the use of di, tri, and tetracyclic acylhydrazide derivatives and analogs, as well as pharmaceutical compositions containing the same, for the treatment or prophylaxis of viral infections and diseases associated therewith, particularly those viral infections and associated diseases caused by the orthopoxvirus. The co-owned U.S. Patent publication 2008/0004452 (published Jan. 3, 2008) further discloses a process for producing ST-246.

Finally, the co-owned PCT publication WO 2011/119698 described that ST-246 can exist in multiple different polymorphic forms. A particular crystalline form of a compound may have physical properties that differ from those of other polymorphic forms and such properties may influence markedly the pharmaceutical processing of the compound and the performance of the resulting dosage form, particularly when the compound is prepared or used on a commercial scale. Such differences may alter the mechanical handling properties of the compound (such as the flow characteristics of the solid material) and the compression characteristics of the compound. Further, the discovery of new polymorphic forms of such pharmaceutically important compound as ST-246, provided a new opportunity to improve the performance characteristics of a pharmaceutical end product and enlarged the repertoire of materials that a formulation scientist has available for designing, for example, a pharmaceutical dosage form of a drug with targeted release profile or other desired physical-chemical properties, such as stability.

New polymorphic forms of a drug substance may display different melting point, hygroscopicity, stability, solubility and/or dissolution rate, crystallinity, crystal properties, bioavailability, toxicity and formulation handling characteristics, which are among the numerous properties that need to be considered in preparing a medicament that can be effectively administered. Furthermore, regulatory agencies require definitive knowledge, characterization and control of the polymorphic form of the active component in solid pharmaceutical dosage forms. Tecovirimat has low solubility in aqueous solutions and hence for efficient oral absorption and efficacy, the drug needs to be micronized to get very fine particles. Fine particle size is usually achieved by milling or micronization. Particle size reduction of tecovirimat monohydrate, however, exhibits dehydration upon micronization. In view of the foregoing, there is a need to have a process that product stable micronized monohydrate. Thus, a rehydration process was developed according to the present invention as described below.

SUMMARY OF THE INVENTION

The present invention provides a method of hydrating ST-246 particles comprising exposing said particles to moisture by conveying volumes of air containing moisture to said particles.

The present invention also provides for reducing the particle size of ST-246 particles comprising:
(a) micronizing ST-246 micronized using an air jet mill in order to reduce particle size to (D90<10 microns) resulting in ST-246 particles that are dehydrated to some extent relative to the ST-246 particles prior to micronization; and
(b) rehydrating said micronized ST-246 particles by exposing said dehydrated particles to moisture by conveying volumes of air containing moisture to said dehydrated particles.

The present invention further provides a method of converting ST-246 polymorph particles exhibiting dehydration to ST-246 polymorph Form I monohydrate particles comprising exposing said partially dehydrated ST-246 polymorph particles to moisture by conveying volumes of air containing moisture to said particles. ST-246 monohydrate polymorph Form I is desirable for its pharmaceutical properties such as stability, lack of hygroscopicity, and processability.

DETAILED DESCRIPTION OF THE INVENTION

Described herein are processes for producing ST-246. The chemical name for ST-246 is N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide and has the following formula:

ST-246

Definitions

In accordance with this detailed description, the following abbreviations and definitions apply. It must be noted that as used herein, the singular forms "a," "an," and "the" include plural referents unless the context clearly dictates otherwise.

The term "polymorphic form, polymorph, polymorph form, crystalline form, physical form or crystalline polymorph" of ST-246 in the present invention refers to a crystal modification of ST-246, which can be characterized by analytical methods such as X-ray powder diffraction pattern (XRPD), differential scanning calorimetry (DSC), by its melting point analysis, or Infrared Spectroscopy (FTIR), or polarized light microscopy.

The term "hydrate" as used herein means a compound or a salt thereof that further includes a stoichiometric or non-stoichiometric amount of water bound by non-covalent intermolecular forces. The term monohydrate as used herein refers to crystal forms formed by the combination of one molecule of water with one molecule of the substance in which the water retains its molecular state as $H_2O$, such combinations being able to form one or more hydrate polymorph. The term "hemihydrate" as used herein refers to a solid with 0.5 molecule of $H_2O$ per molecule of the substance.

The term "pharmaceutical composition" or "pharmaceutical formulation" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions of the present invention encompass any composition made by admixing the active ingredient, active ingredient dispersion or composite, additional active ingredient(s), and pharmaceutically acceptable excipients.

PCT publication WO 2011/119698 discloses 6 polymorphs or crystal structures for ST-246 with various degrees of hydration. Form I of ST-246 is a monohydrate form that shows an X-ray powder diffraction pattern having characteristic peaks of about 7.63, 10.04, 11.47, 14.73, 15.21, 15.47, 16.06, 16.67, 16.98, 18.93, 19.96, 20.52, 20.79, 22.80, 25.16, 26.53, 27.20, 27.60, 29.60, 30.23, 30.49, 30.68, 31.14, 33.65, 34.33, 35.29, 35.56, 36.30, 37.36, 38.42, 38.66 degrees.

Polymorphs Forms II and IV are anhydrate crystalline forms of ST-246. Anhydrate Form IV is relatively unstable when exposed to ambient conditions and prone to conversion to Form V, due to absorption of moisture.

Form V is a hemihydrate crystalline form of ST-246. Examples of XRPD data for Form V are shown below:

| Angle 2-Theta ° | d value Angstrom | Intensity Cps | Intensity % |
|---|---|---|---|
| 6.39 | 13.81 | 101 | 100.0 |
| 6.72 | 13.14 | 9.56 | 9.5 |
| 8.16 | 10.82 | 1.88 | 1.9 |
| 9.04 | 9.78 | 3.75 | 3.7 |
| 9.52 | 9.28 | 6.38 | 6.3 |
| 10.52 | 8.41 | 4.88 | 2.1 |
| 12.40 | 7.13 | 5.06 | 5.0 |
| 12.79 | 6.92 | 7.31 | 7.3 |
| 13.38 | 6.61 | 4.13 | 4.1 |
| 14.15 | 6.25 | 12.0 | 11.9 |
| 14.57 | 6.07 | 11.4 | 11.4 |
| 15.84 | 5.59 | 15.9 | 15.9 |
| 16.32 | 5.43 | 10.7 | 10.6 |
| 16.67 | 5.31 | 25.7 | 25.6 |
| 17.50 | 5.06 | 21.2 | 21.1 |
| 18.13 | 4.89 | 9.19 | 9.1 |
| 18.48 | 4.80 | 5.44 | 5.4 |
| 18.78 | 4.72 | 16.9 | 16.8 |
| 19.79 | 4.48 | 38.3 | 38.1 |
| 20.68 | 4.29 | 17.3 | 17.2 |
| 21.07 | 4.21 | 13.9 | 13.8 |
| 21.54 | 4.12 | 5.25 | 5.2 |
| 22.01 | 4.04 | 5.81 | 5.8 |
| 22.73 | 3.91 | 7.50 | 7.5 |
| 23.60 | 3.77 | 6.38 | 6.3 |
| 25.25 | 3.52 | 4.50 | 4.5 |
| 25.73 | 3.46 | 20.1 | 20.0 |
| 26.27 | 3.39 | 3.94 | 3.9 |
| 26.73 | 3.33 | 5.63 | 5.6 |
| 27.24 | 3.27 | 13.3 | 13.2 |
| 29.02 | 3.07 | 10.1 | 10.1 |
| 29.50 | 3.03 | 8.06 | 8.0 |
| 29.83 | 2.99 | 6.94 | 6.9 |
| 30.44 | 2.93 | 9.00 | 9.0 |
| 32.04 | 2.79 | 4.50 | 4.5 |
| 33.52 | 2.67 | 7.13 | 7.1 |
| 34.84 | 2.57 | 4.69 | 4.7 |

| Angle 2-Theta ° | d value Angstrom | Intensity Cps | Intensity % |
|---|---|---|---|
| 35.68 | 2.51 | 6.19 | 6.2 |
| 39.78 | 2.26 | 4.31 | 4.3 |

It has been reported that air jet milling of hydrates of organic compounds to reduce particle size can lead to dehydration (Kang, F., Cryst. Growth Des. 2012, 12, 60-74; and Ito, S. J. Pharm. Sci, 1996, 85, 1117-1122). Dehydration may be directly caused by exposure of the drug substance to the very dry compressed air used for air jet milling. In addition, reduction in particle size may allow moisture to be removed from the crystal more readily. Air-jet milling is generally considered to involve the least mechanical/thermal stress to the API compared to other techniques, and other techniques are unlikely to be suitable for particle size reduction to less than 10 microns. SIGA discovered that ST-246 Form I monohydrate can become dehydrated as a result of air jet milling, based on precise determinations of water content.

The ST-246 drug substance manufacturing process consistently produces ST-246 monohydrate (polymorph Form I). ST-246 monohydrate is micronized using an air jet mill in order to reduce particle size (D90<10 microns) as required for acceptable bioavailability. After scale-up of the micronization process to commercial scale, the micronized Form I was found to partially convert to hemihydrate polymorph Form V upon storage under certain conditions. The root cause was determined to be dehydration of the monohydrate Form I during micronization. When stored with limited exposure to ambient air, the dehydrated material can convert to the hemi-hydrate Form V. This was unexpected, as ST-246 monohydrate is nonhygroscopic over the relative humidity (RH) range of 10-90% and only undergoes dehydration at very low RH (<3-6% RH). In the present invention, methods to re-introduce moisture into the dehydrated ST-246 molecule are disclosed in order to rapidly obtain the desired monohydrate moisture level, thereby preventing conversion to Form V upon storage.

Surprisingly, dehydrated micronized ST-246 monohydrate absorbs moisture, so rehydration is feasible at humidity levels present in ambient air. Rehydration of partially dehydrated ST-246 to the monohydrate level has been successfully demonstrated on a commercial scale as indicated in the examples below. Preferably, rehydration can be carried out using a technique selected from: Turboscreen; High Shear Granulator; Tray Drying; Vibratory sifter/sieve; Mixer/blender; and Fluid bed dryer. This technique can be used for other substances that undergo dehydration upon micronization.

Accordingly, the present invention provides a method of hydrating ST-246 particles comprising exposing said particles to moisture by conveying volumes of air containing moisture to said particles. Preferably, the hydrated ST-246 is micronized ST-246 polymorph monohydrate (Polymorph Form I). Preferably, the exposure of ST-246 particles to moisture takes place during a process selected from the group consisting of: Turboscreen, High Shear Granulator, Tray Drying, Vibratory sifter/sieve, Mixer/blender, and Fluid bed dryer, more preferably High Shear Granulator, most preferably Turboscreen.

The present invention also provides a method for reducing the particle size of ST-246 particles comprising: (a) micronizing ST-246 using an air jet mill in order to reduce particle size to (D90<10 microns) resulting in partially dehydrated ST-246 particles relative the ST-246 particles prior to micronization; and (b) rehydrating said micronized ST-246 particles by exposing said dehydrated particles to moisture by conveying volumes of air containing moisture to said dehydrated particles. Preferably, the ST-246 prior to micronization is ST-246 monohydrate (Polymorph Form I). Preferably, the micronization step is carried out at a humidity of less than about 60% RH, more preferably less than about 40% RH).

The present invention also provides for a method of converting ST-246 polymorph particles to ST-246 polymorph monohydrate particles comprising exposing said ST-246 polymorph particles to moisture by conveying volumes of air containing moisture to said particles. Preferably, the methods of the present invention further prevent the conversion of ST-246 polymorph particles to ST-246 polymorph hemihydrate particles (ST-246 Polymorph Form V).

The benefit of the rehydration is improved solid-form stability, and therefore shelf-life, of micronized ST-246 monohydrate. Without the rehydration process, it would not be possible to consistently produce micronized ST-246 monohydrate at commercial scale, without partial conversion to Form V during storage. The equipment described in this invention is common and readily available, and can easily be used to rehydrate ST-246 without modification. The TurboScreen process is high-yielding. After five passes through the equipment, only 3-4% of material is lost. No significant change in particle size distribution has been observed after the TurboScreen process.

More details about the Turboscreen, High Shear Granulator, and Tray Drying processes are provided below.

Vibratory Sifter/Sieve:

Typical applications include sifting, scalping, classifying, de-dusting and de-lumping of dry bulk solids. Vibration causes particles to pass through a screen. When done in an atmosphere of humidified air, this allows exposure of product to moisture.

Mixer/Blender:

Several blender types (including tumble and ribbon) could be used for rehydration according to the present invention. Blender movements (rotation or inversion) increase the mobility of the individual particles and thus promote diffusive blending. Diffusion blending occurs where the particles are distributed over a freshly developed interface. Since the blender is rotating, the air/bed interface is constantly renewing. In the absence of segregating effects, the diffusive blending will in time lead to a high degree of homogeneity. V-Blenders are therefore preferred when precise blend formulations are required. They are also well suited for applications where some ingredients may be as low as one percent of the total blend size. A V-blender could be modified to humidify API if the intensifier bar were replaced with a perforated tube for humid air injection during tumbling. However, a method of venting the blender would need to be devised such that material would not be lost when the vent points down.

Fluid Bed Dryer:

Fluid bed dryers could be used for rehydration according to the present invention. This would be an efficient method, due to fluidization of solid material in a large volume of air.

Rehydration of Micronized Product:

Since dehydration was concluded to be the driver for formation of hemihydrate Form V upon storage of micronized ST-246 monohydrate, a rehydration process has been developed to increase the moisture level of the partially dehydrated material to the monohydrate moisture level.

DVS studies indicated that dehydrated ST-246 monohydrate rapidly absorbs moisture, so rehydration is feasible at humidity levels present in ambient air. The rehydration process utilizes a Sweco Turbo-Screen. The Turbo-Screen uses large volumes of room air to convey the product through a screen, and is therefore an efficient way to expose the product to moisture. The screen pore size is selected such that no particle size discrimination of the ST 246 API is expected. To ensure a consistent, robust rehydration process, the relative humidity in the processing suite will be controlled at 40 60% RH.

Turbo-Screen rehydration feasibility studies have been performed, and are discussed below. These studies were conducted using micronized material Commercial scale unmicronized ST-246 monohydrate (commercial validation batch SG 10A11 Q) was micronized using a commercial scale 30" mill and processed through a pilot scale Turbo-Screen. The effect of multiple passes (up to 5) of material through the Turbo-Screen was evaluated. Data from the trial are summarized in Table-1. The Turbo-Screen process was found to effectively increase moisture content from 4.0 4.5%. Material collected before and after the Turbo-Screen process was placed on an informal accelerated stability study, in sealed aluminum pouches staged at 37 40° C. and 50° C. XRPD results from this study to date are summarized in Table-2.

TABLE 1

Summary of Turbo-Screen Feasibility Study 5665/5677

| Test | Trial 5665 Freshly Micronized | Trial 5677 Turbo-Screen (5 Passes) |
|---|---|---|
| Particle Size (D90; microns) | 4.0 | 4.0 |
| Moisture Content (KF) | 4.0% | 4.5% |

TABLE 2

Informal Stability Study on Turbo-Screen Feasibility Study 5665/5677 (XRPD Results)

| Storage Condition/Time | Trial 5665 - Freshly Micronized | Trial 5677 Turbo-Screen (5 Passes) |
|---|---|---|
| 37-40° C. | | |
| 11 days | Form V present[a] | Not Tested |
| 1 month | Form V present | Conforms to Form I, Form V not detected |
| 6 months | Not Tested | Conforms to Form I, Form V not detected |
| 50° C. | | |
| 2 weeks | Not Tested | Conforms to Form I, Form V not detected |

[a]Form V in sample shown by presence of reflections in XRPD diffractogram at ~6.3 and 14.1 degrees 2-theta.

Stability Studies:

After 6 months at 37 40° C., and 2 weeks at 50° C., the material rehydrated via Turbo-Screen has not shown the presence of hemihydrate Form V. The freshly micronized material showed Form V after just 11 days at 37 40° C. The particle size of this material was smaller than product typically produced in the commercial scale mill (D90 of ~4 microns rather than ~6 microns) due to the lower feed rate used during this trial (~50 kg/hr rather than 100 kg/hr during typical processing).

Turbo-Screen Optimization Study—Study 5707:

Material micronized was processed through a commercial scale Turbo-Screen for up to five passes. Results are summarized in Table 3. During these trials, the humidity in the processing suite was increased using a portable room humidifier and ranged from approximatly 28 58% RH. Powdersize is upgrading its HVAC system to control humidity of the processing suite at 40 60% RH, and this system will be qualified prior to validation of the rehydration process.

TABLE 3

Summary of Micronization and Turbo-Screen Optimization Study 5707

| Trial | Mill Pressure (psi) | Feed Rate (kg/hr) | Moisture Content % (SIGA) | Moisture Content % (Powdersize) | Particle Size (D90; microns) |
|---|---|---|---|---|---|
| Trial 1 - Freshly Micronized (FM) | 115 | 100 | 4.3 | 4.4 | 7.6 |
| Trial 1 - Turbo-Screen Pass 1 (TS-1) | Turbo-Screen Feed Rate: 100 kg/hr | | 4.5 | 4.5 | 7.6 |
| TS-2 | | | 4.6 | 4.6 | 7.6 |
| TS-3 | | | 4.6 | 4.5 | 7.3 |
| TS-4 | | | 4.6 | 4.5 | 8.3 |
| TS-5 | | | 4.6 | 4.6 | 7.8 |
| Trial 2-FM | 115 | 160 | 4.3 | 4.3 | 8.7 |
| TS-1 | Turbo-Screen Feed Rate: 100 kg/hr | | Not Tested | 4.5 | 8.4 |
| TS-2 | | | 4.6 | 4.6 | 8.7 |
| TS-3 | | | 4.7 | 4.5 | 8.5 |
| Trial 4-FM | 105 | 60 | 4.0 | 4.2 | 6.2 |
| TS-1 | Turbo-Screen Feed Rate: 100 kg/hr | | 4.5 | 4.4 | 5.9 |
| TS-2 | | | 4.6 | 4.5 | 6.7 |
| TS-3 | | | 4.5 | 4.6 | 7.0 |
| TS-4 | | | 4.6 | 4.5 | 6.3 |
| TS-5 | | | 4.7 | 4.5 | 6.5 |
| Trial 5-FM | 115 | 75 | 4.2 | 4.2 | 6.7 |
| TS-1 | Turbo-Screen Feed Rate: 100 kg/hr | | 4.6 | 4.5 | 7.3 |
| TS-2 | | | 4.6 | 4.6 | 7.2 |
| TS-3 | | | 4.7 | 4.6 | 7.6 |
| TS-4 | | | 4.7 | 4.5 | 7.4 |
| TS-5 | | | 4.7 | 4.6 | 7.1 |
| Trial 6-FM | 115 | 75 | 4.1 | 4.1 | 6.5 |
| TS-1 | Turbo-Screen Feed Rate: 200 kg/hr | | 4.5 | 4.5 | 6.3 |
| TS-2 | | | 4.6 | 4.5 | 6.8 |
| TS-3 | | | 4.6 | 4.5 | 6.7 |
| TS-4 | | | 4.6 | 4.6 | 6.7 |
| TS-5 | | | 4.6 | 4.6 | 6.7 |

These results show that the Turbo-Screen process can successfully rehydrate the micronized material to a level consistent with the monohydrate (theoretical value of 4.57%). The Turbo Screen rehydration process does not cause any significant change to particle size of the product.

Example 1—ST-246 Rehydration Using Turboscreen

Turboscreening is typically used to remove a small fraction of oversized particles from large quantities of a bulk material. The Turbo-Screen uses large volumes of atmosphere air to convey the product through a screen, and is therefore an efficient way to expose the product to moisture. The screen pore size is selected to minimize particle size discrimination of ST-246. To ensure a consistent, robust rehydration process, the relative humidity in the processing suite is controlled at >30%% RH. Material that has been passed through the Turboscreen equipment either 3, 4, or 5 passes has shown a good stability profile, as evidenced by lack of formation of hemihydrate Form V.

Micronized API particles freely mix with the rapidly moving humidified air before encountering a tensile bolt cloth mesh screen that breaks up lumps; further exposing the API to moist air. The humidified micronized material is then separated from the airstream in a cyclone and discharged to drums. Multiple separate passes were employed through the Turboscreen to ensure that the micronized API has been rehydrated to the monohydrate moisture level. Screens are continually swept with a rotating wand utilizing high pressure air to clean the screen and maintain high throughput. These are commercially feasible processes with no change in the physical properties of the particles such as particle size distribution, bulk and tap densities.

Experimental Procedure

The equipment used for micronization and hydration are the following: A 30" OD/24" ID Spiral pancake Jet Mill equipped with a Volumetric Single Screw Auger Feeder w/60 mm flights and a 30" Sweco Turbo-Screen respectively Unmicronized ST-246 was micronized at a Feed rate of 60 to 200 kg/hour and a mill pressure of 95 to 115 psi. The particle size is monitored during the micronization process using dynamic laser light measurements. The feed rate and the mill pressure was optimized to give product with optimal particle size. Rehydration was done using the Turbo-screen with feed rates up to approximately 200 kg/hr. However lower feed rates could provide more efficient rehydration, due to better exposure to air inside the equipment. Materials have been Turbo-Screened by passing through the Turbo screen with more than 1 passes. These materials have shown good chemical and polymorphic stability profile. Rehydration has been successful with processing suite humidity levels as low as 30% to 60% RH. Tecovirimat monohydrate does not continue to absorb moisture once fully hydrated, so there is no risk of over-hydration.

Example 2—ST-246 Rehydration Using High Shear Granulator

High shear granulation is typically used to agglomerate small particles together by the addition of a binder solution to a stirred vessel of particles and powders with blades driven by powerful motors. The bottom blade, the plow, turns slowly to force moistened particles into intimate contact with each other while driving out air. The smaller vertical chopper blade spins rapidly to break up lumps that form. To use for humidification, the blades would both be spinning rapidly to keep the particle bed fluffed up while moist air was forced into the bowl—preferably near the bottom of the bed and through multiple inlets. A filter at the top of the unit prevents particle escape while allowing for air passage.

Experimental Procedure

A 3 to 5 kg batch of micronized ST-246 drug substance (form I) is charged into a High Shear Granulator VG 25. The granulator lid is closed while keeping open the exhaust filter port and the Inspection window. The ST-246 is hydrated using an external source of moist air with mixing in the VG 25 and with the blade speed set to 25 rpm and, cork screw at 0 rpm i.e power off for a period of several hours. The moisture content of the ST-246 was determined using the Karl fisher method for moisture determination. The theoretical moisture content for ST-246 monohydrate is 4.54% w/w.

The ST-246 drug substance that underwent hydration using the above process was analyzed for moisture content, particle size, and polymorphic stability studies using XRPD. The results are summarized below:

| Sample | Moisture content (% w/w) | PSD (D90, D50 and D10 in microns) |
| --- | --- | --- |
| Before granulator humidification | 4.17 | 4.1, 1.8, 1.2 |
| After granulator humidification | 4.48, 4.52 | 4.2, 2.4, 1.4 |
| XRPD of Humidified sample stored 1 wk at 50° C. | Conforms to Form I, showed no polymorphic Form V. | |

These results indicate that:
1. Freshly micronized ST-246 can be hydrated to its monohydrate state using High shear granulator, with no changes in the particle size distribution.
2. Accelerated stability studies (at 50° C.) showed the polymorphic stability of Form I and absence of formation of Form V.

Example 3—ST-246 Rehydration Using Tray Drying

Tray drying is typically used to dry a product. However, the cabinet equipment could be modified to provide a moist environment rather than a dry one. As the name implies, material is spread over open trays and exposed to the atmosphere. In the pharmaceutical industry, the atmosphere is usually controlled for both temperature and relative humidity and includes fans to evenly expose the trays. Depth of the product in the trays determines whether the humidification/dehumidification is even through the product. Tray systems have been devised that are continuous in operation such that the material would be much more homogeneous in moisture content upon exiting.

Experimental Procedure

1) Thirty grams of partially dehydrated micronized ST-246 was spread in a tray and placed on a benchtop under ambient temperature and a humidity of 20-30%, 2) one gram of partially dehydrated micronized ST-246 was spread in a tray and placed on A stability chamber with controlled temperature and humidity at 25° C./60% RH and 3) one gram of partially dehydrated micronized ST-246 was spread in a tray and placed on a stability chamber with controlled temperature and humidity at 40° C./75% RH. After 18 hours at bench top or 2 hours at 25° C./60% RH or 2 hours at 40° C./75% RH, the moisture content of ST-246 was determined using Karl Fisher method for moisture determination. These results showed that ST-246 API was re-hydrated to moisture levels at ~4.5% and confirmed by XRPD data to be Form I. Furthermore, the humidified API demonstrated polymorphic stability when packaged in sealed aluminum bag and staged at 37° C. for 3 months. These results suggest that freshly micronized ST-246 can be rehydrated by exposing to atmosphere at different humidity level and the rehydrated ST-246 shows polymorphic stability. The results are summarized below.

| Sample | Moisture (% w/w KF) | XRPD | DSC (° C.) | SEM |
|---|---|---|---|---|
| Freshly Micronized | NA | Form I | 129.7, 195.9 | No Change in particle |
| Hydration and sealed aluminum bag stored at 37° C. for 3 months. | ~4.5% | Form I: Showed no Form V. | 128.9, 196.7 | morphology |

All references cited herein are herein incorporated by reference in their entirety for all purposes.

The invention has been described in terms of preferred embodiments thereof, but is more broadly applicable as will be understood by those skilled in the art. The scope of the invention is only limited by the following claims.

What is claimed is:

1. A method for reducing the particle size of 4-trifluoromethyl-N-(3,3a,4,4a,5,5a,6,6a-octahydro-1,3 -dioxo -4,6 -ethenocycloprop[f]isoindol-2(1H)-yl)-benzamide (ST-246) particles that have been dehydrated during a micronization process comprising:

(a) micronizing polymorph Form I monohydrate ST-246 particles using an air jet mill in order to reduce particle size to (D90<10 microns) to obtain partially dehydrated ST-246 polymorph Form I particles and/or ST-246 polymorph Form V hemihydrate particles; and (b) rehydrating said micronized ST-246 particles by exposing said particles to moisture by conveying volumes of air having greater than 30% relative humidity to said particles.

2. The method of method of claim 1, wherein the exposure of ST-246 particles to moisture takes place during a process selected from the group consisting of: high-throughput forced air, screen-dependent classification, High Shear Granulation, Tray Drying, sifting, scalping, classifying, de-dusting or de-lumping using a Vibratory sifter/sieve, increasing the mobility of the particles using a Mixer/blender, and Fluid bed drying.

3. The method of claim 1, wherein the exposure of ST-246 particles to moisture takes place during the process of high-throughput forced air, screen-dependent classification.

4. The method of claim 1, wherein the exposure of ST-246 particles to moisture takes place during the process of high shear granulation.

5. The method of claim 1, wherein the micronized ST-246 particles contain no ST-246 polymorph Form V hemihydrate particles.

* * * * *